US012678344B2

(12) United States Patent
Moritani

(10) Patent No.: US 12,678,344 B2
(45) Date of Patent: Jul. 14, 2026

(54) DISPOSABLE WEARABLE ARTICLE

(71) Applicant: DAIO PAPER CORPORATION, Ehime (JP)

(72) Inventor: Akie Moritani, Ehime (JP)

(73) Assignee: DAIO PAPER CORPORATION, Ehime (JP)

( * ) Notice: Subject to any disclaimer, the term of this patent is extended or adjusted under 35 U.S.C. 154(b) by 536 days.

(21) Appl. No.: 18/040,239

(22) PCT Filed: Aug. 20, 2021

(86) PCT No.: PCT/JP2021/030569
§ 371 (c)(1),
(2) Date: Jul. 27, 2023

(87) PCT Pub. No.: WO2022/064918
PCT Pub. Date: Mar. 31, 2022

(65) Prior Publication Data
US 2023/0404820 A1 Dec. 21, 2023

(30) Foreign Application Priority Data
Sep. 25, 2020 (JP) ................................. 2020-161080

(51) Int. Cl.
*A61F 13/511* (2006.01)
*A61L 15/20* (2006.01)

(52) U.S. Cl.
CPC ... *A61F 13/51113* (2013.01); *A61F 13/51104* (2013.01); *A61L 15/20* (2013.01); *A61F 2013/51117* (2013.01)

(58) Field of Classification Search
CPC .......... A61F 13/51104; A61F 13/51113; A61F 2013/51066; A61F 2013/51069; A61F 2013/51117; A61L 15/20
See application file for complete search history.

(56) References Cited

U.S. PATENT DOCUMENTS 3,645,264 A * 2/1972 Gallagher ......... A61F 13/51113
604/371
8,865,965 B2 * 10/2014 Sato .................. A61F 13/51113
604/367

(Continued)

FOREIGN PATENT DOCUMENTS

JP 2010075733 A 4/2010
JP 2010526630 A 8/2010

(Continued)

OTHER PUBLICATIONS

International Search Report for PCT/JP2021/030569, dated Nov. 2, 2021.

*Primary Examiner* — Catharine L Anderson
(74) *Attorney, Agent, or Firm* — Andrus Intellectual Property Law, LLP

(57) ABSTRACT

The disposable wearable article enhances effects obtained from application of hydrophilic lotion to the top sheet of the article. The disposable wearable article includes a top sheet having a skin-touching region that is brought into contact with skin of a wearer, and an underside member adjacent to an underside of the top sheet, wherein the top sheet is made of liquid-pervious nonwoven fabric, wherein the skin-touching region has a lotion-bearing zone which bears a water-containing hydrophilic lotion, wherein the top sheet has in its under face a plurality of dents hollowed toward a top side of the top sheet and arranged at intervals, wherein a upper surface of each dent and the underside member are spaced apart from each other with a gap therebetween, and wherein the lotion-bearing zone at least partly overlaps one or more of the dents.

19 Claims, 13 Drawing Sheets

(56)            References Cited

U.S. PATENT DOCUMENTS

| 12,329,621 | B2 * | 6/2025 | Lang ...................... D21H 27/40 |
| 2003/0167043 | A1 | 9/2003 | Roe et al. |
| 2004/0158216 | A1 * | 8/2004 | Kasai .................. A61F 13/8405 |
| | | | 604/367 |
| 2006/0135920 | A1 * | 6/2006 | Virgilio ............... A61F 13/8405 |
| | | | 604/359 |
| 2008/0249491 | A1 * | 10/2008 | Young .................. A61K 8/4973 |
| | | | 604/385.01 |
| 2008/0287896 | A1 | 11/2008 | Vega et al. |
| 2015/0231000 | A1 | 8/2015 | Uda |
| 2017/0312144 | A1 | 11/2017 | Moritani |

FOREIGN PATENT DOCUMENTS

| JP | 2013233311 A | 11/2013 |
| JP | 2014068948 A | 4/2014 |
| JP | 2016096926 A | 5/2016 |
| JP | 2017153915 A | 9/2017 |
| JP | 2020146133 A | 9/2020 |

* cited by examiner

[FIG.1]
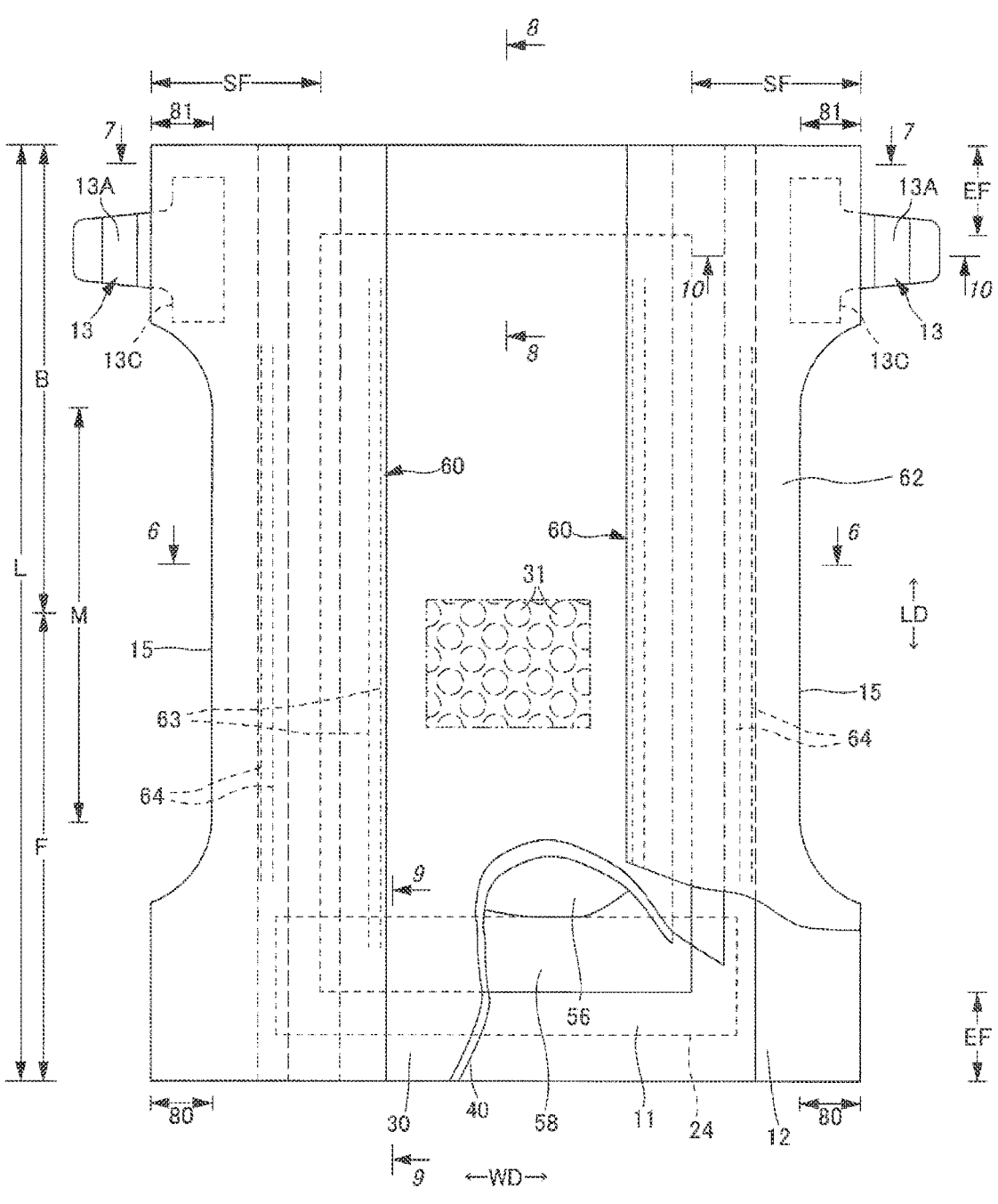

[FIG.2]
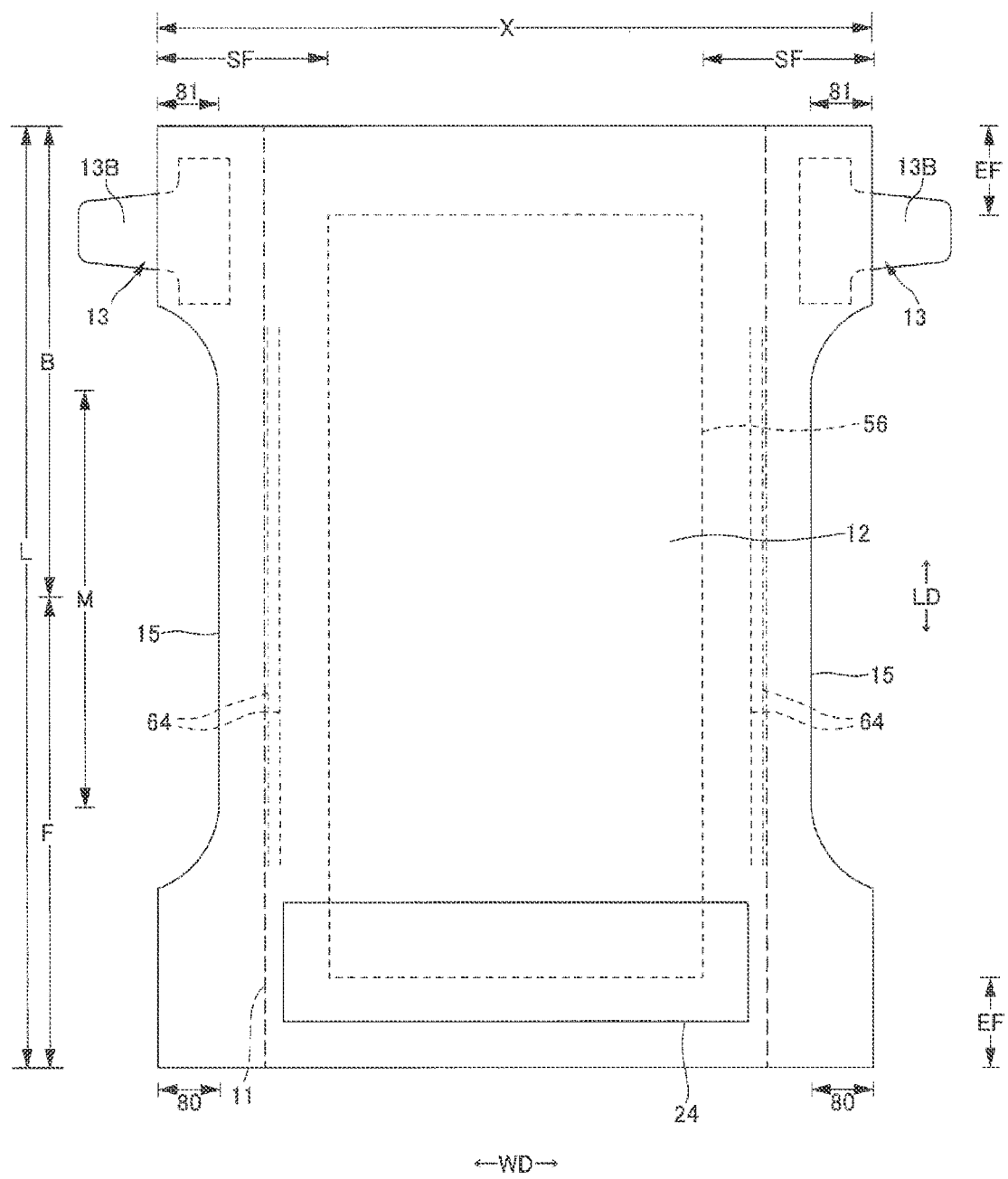

[FIG.3]
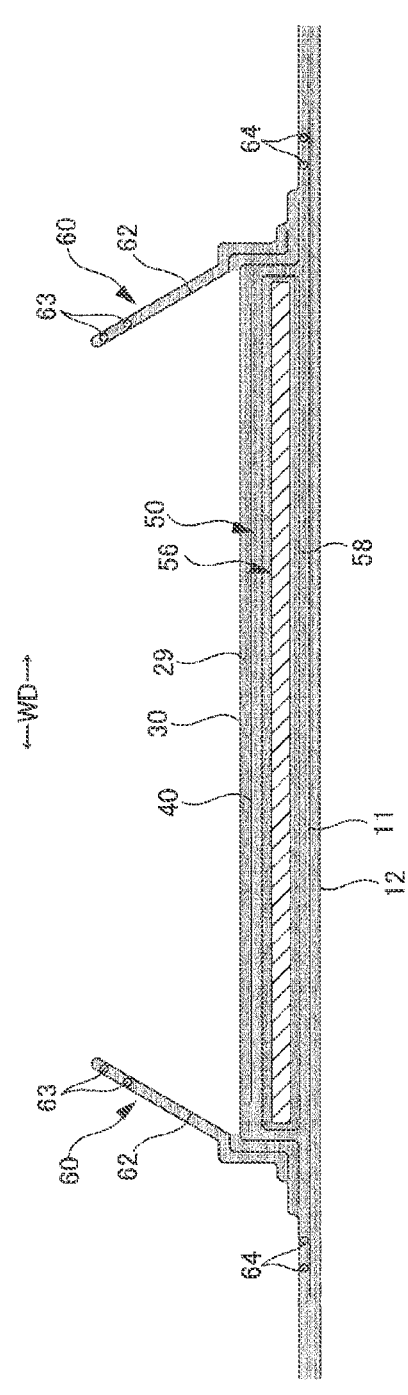

[FIG.4]
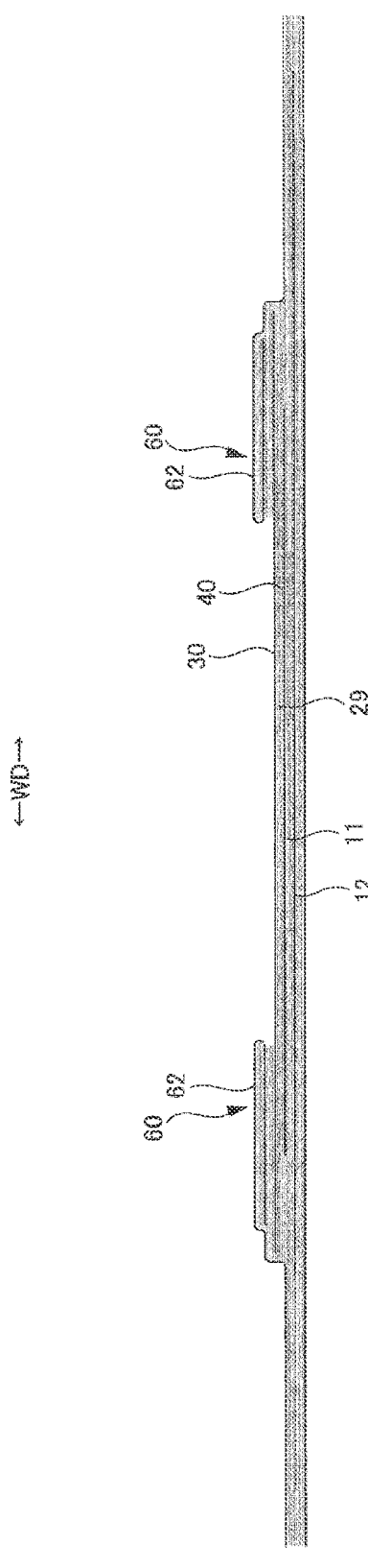

[FIG.5]
(a)
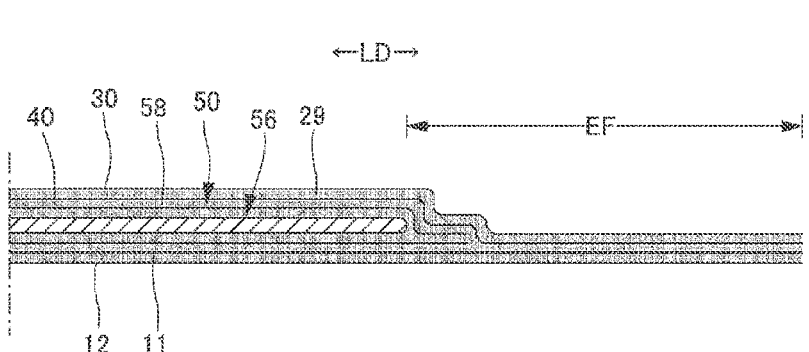
(b)
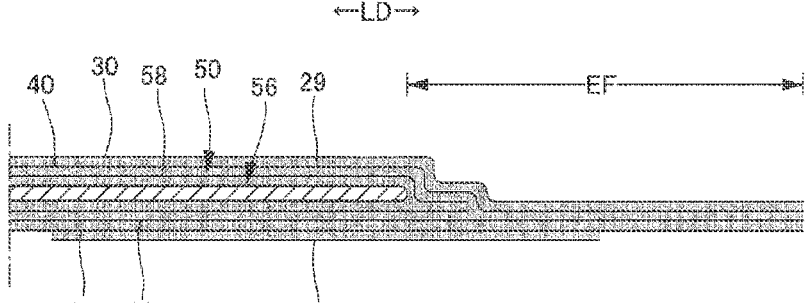
(c)
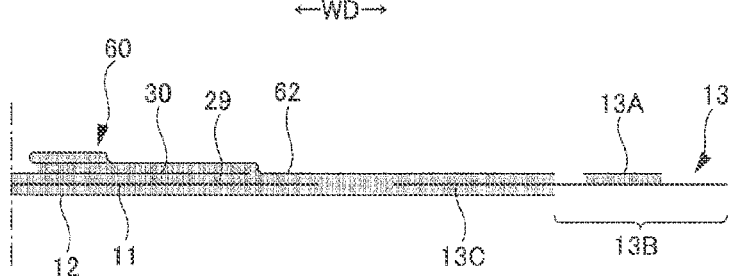

[FIG.6]
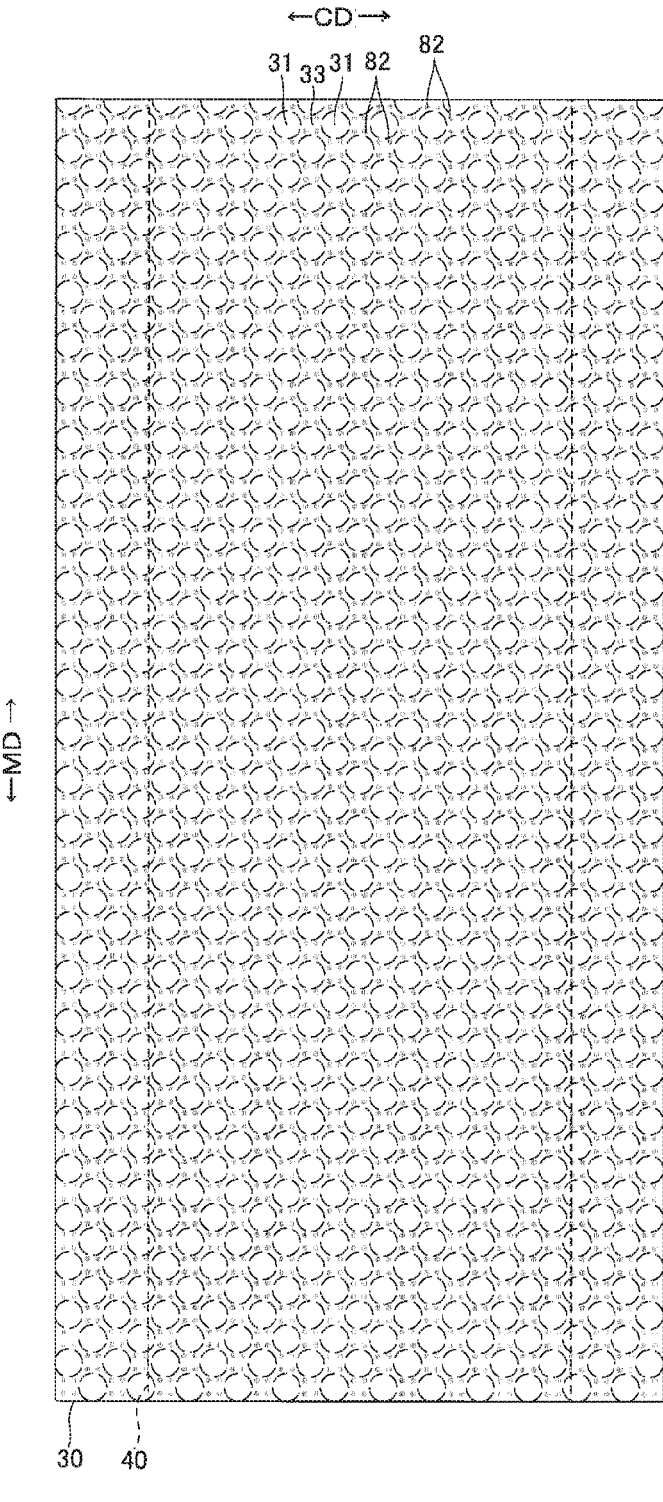

[FIG.7]
(a)
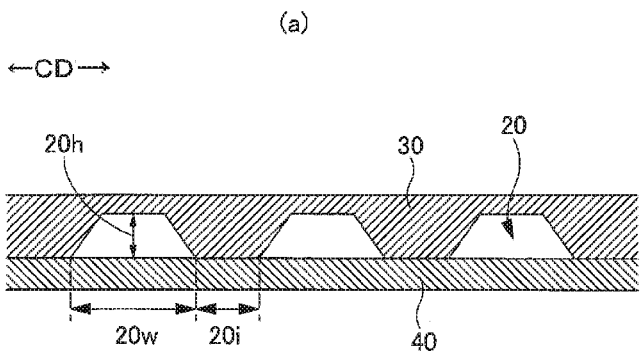
(b)
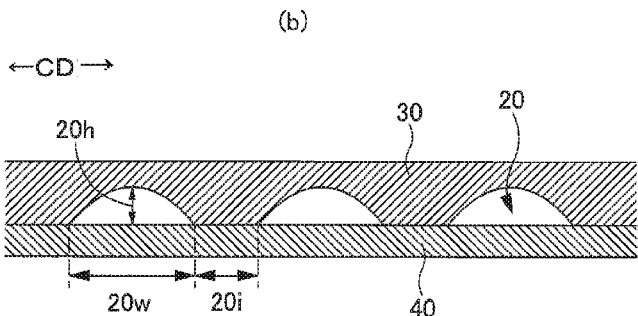
(c)
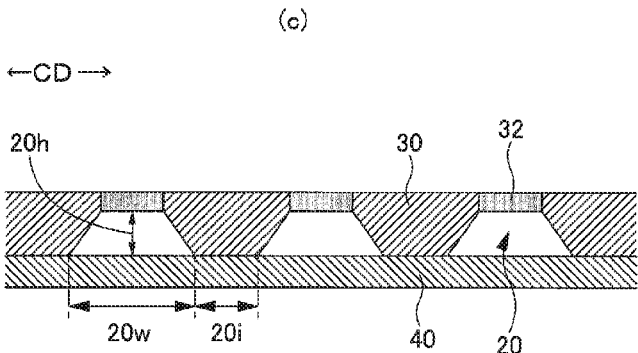

[FIG.8]
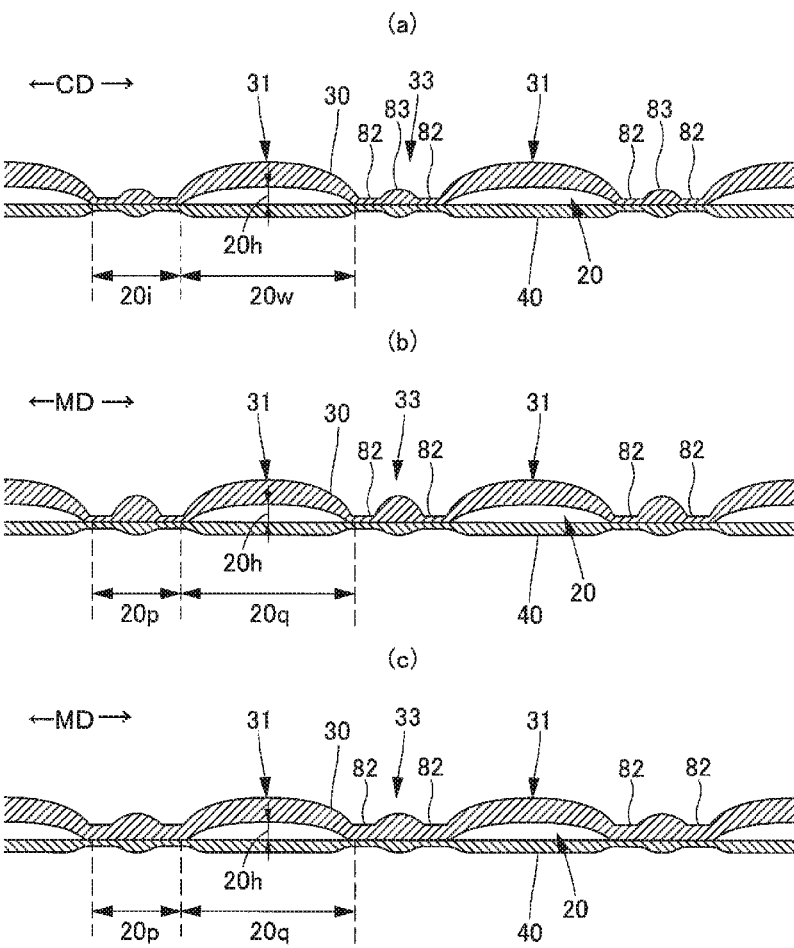

[FIG.9]
(a)
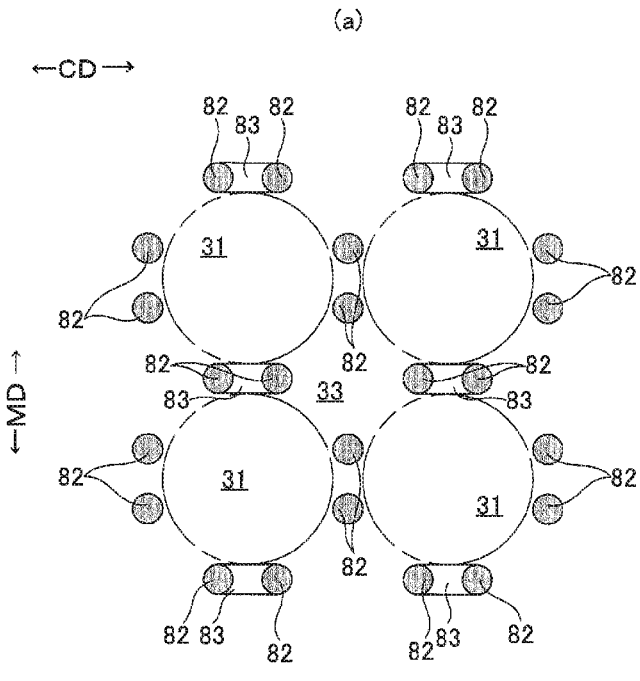
(b)
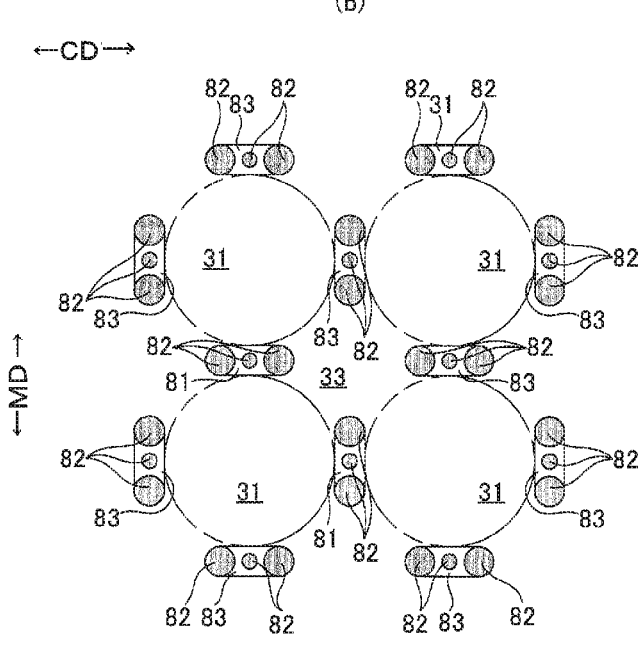

[FIG.10]
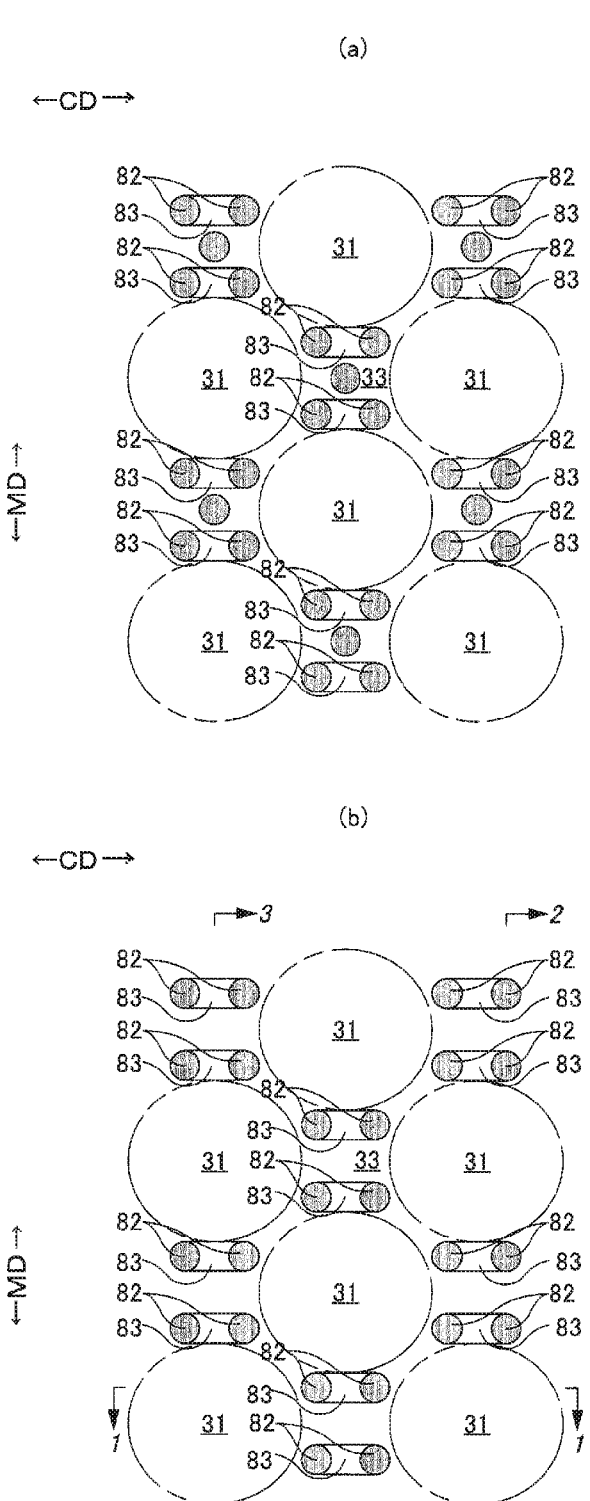

[FIG.11]
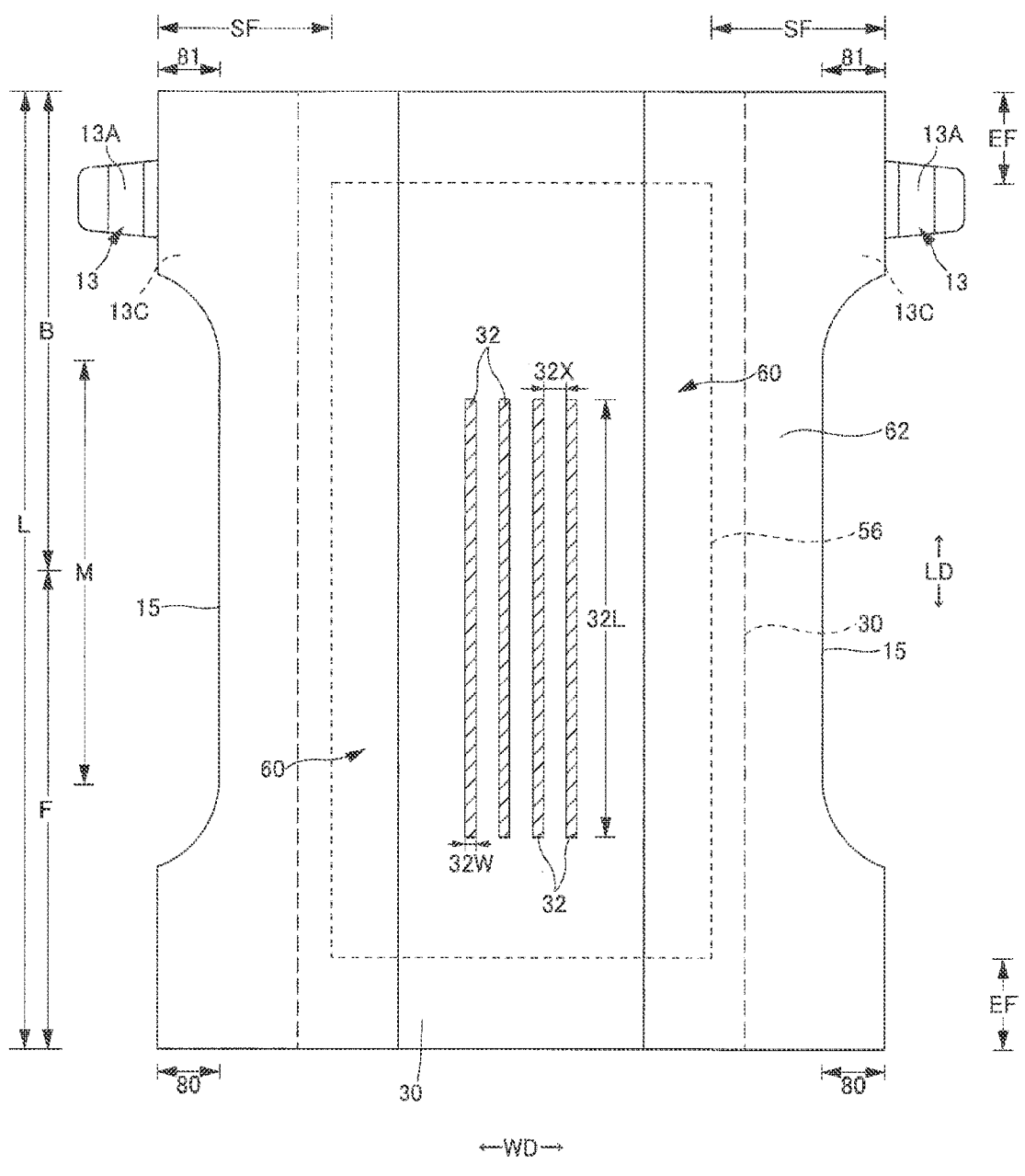

[FIG.12]
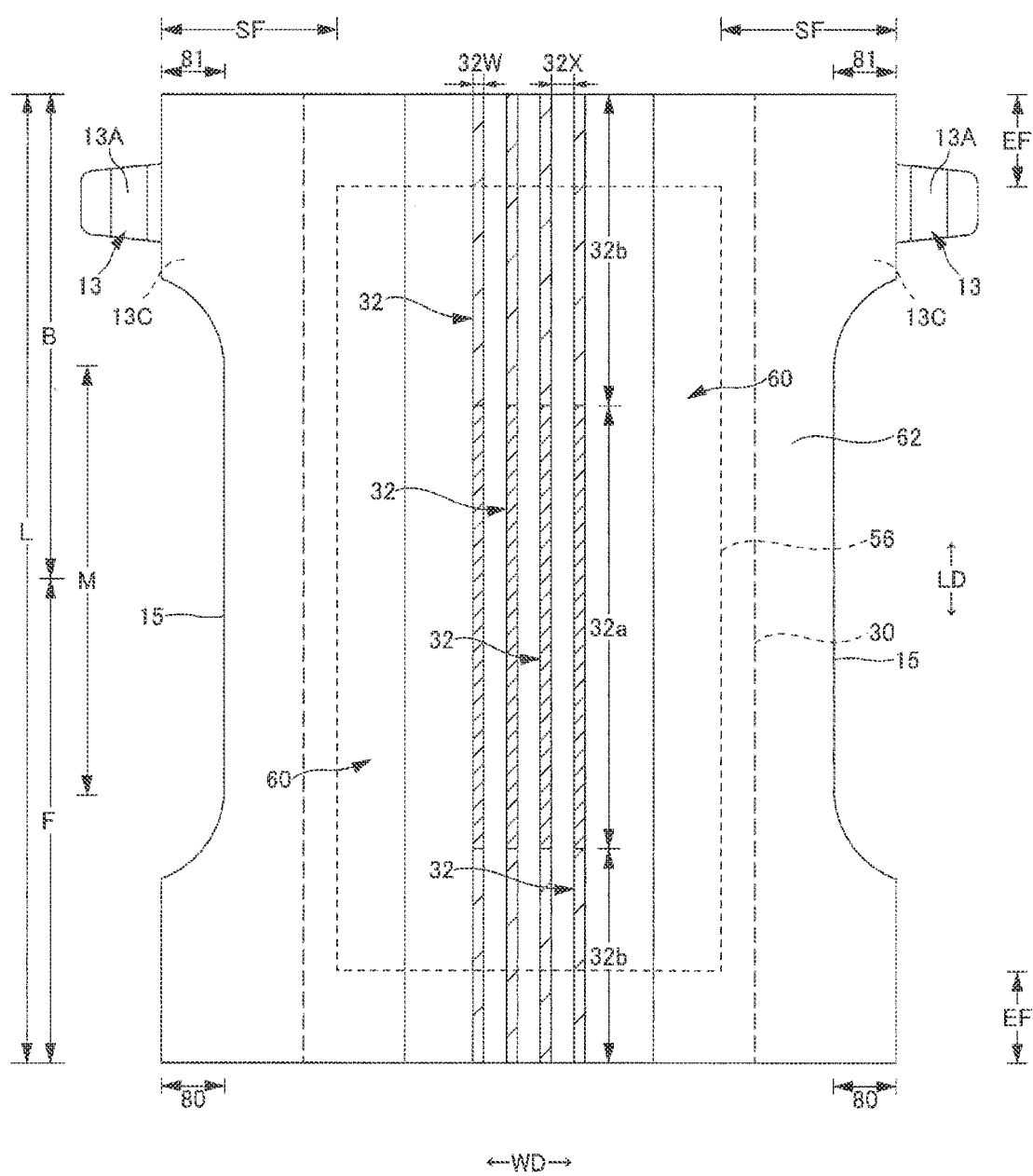

[FIG.13]
(a)
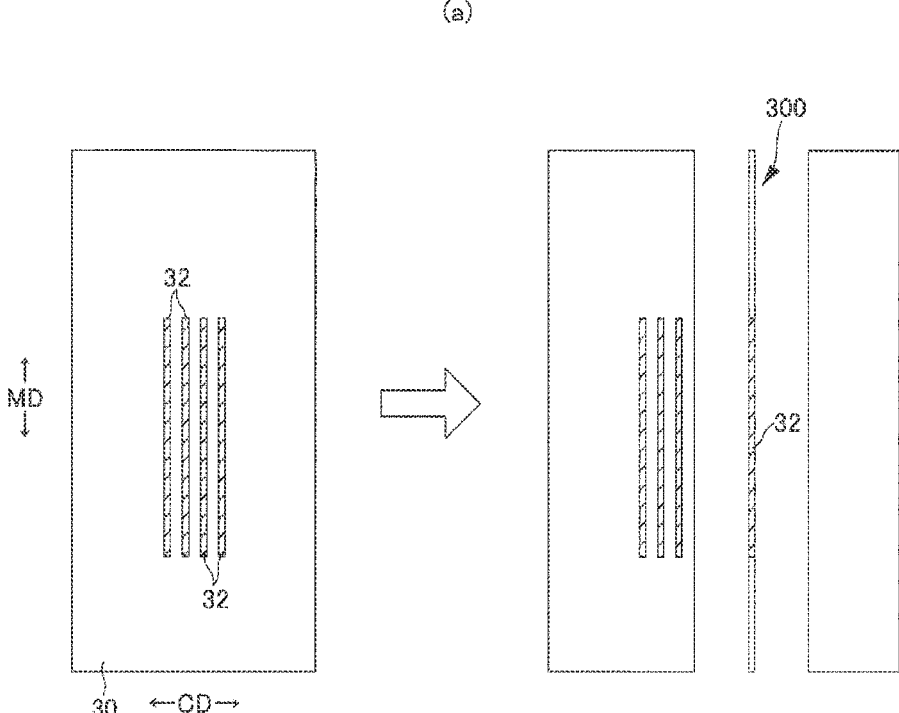
(b)

DISPOSABLE WEARABLE ARTICLE

CROSS-REFERENCE TO RELATED APPLICATIONS

This application is the U.S. national stage application of International Application PCT/JP2021/030569, filed Aug. 20, 2021, which international application was published on Mar. 31, 2022, as International Publication WO 2022/064918 in the Japanese language. The International Application claims priority of Japanese Patent Application No. 2020-161080, filed Sep. 25, 2020. The international application and Japanese application are both incorporated herein by reference, in entirety.

TECHNICAL FIELD

The present invention relates to disposable wearable articles, including disposable diapers and sanitary napkins.

BACKGROUND ART

Disposable wearable articles, in particular, disposable diapers, often pose skin problems, particularly, skin rash of wearers. Such problems may result from physical irritation (friction or coarseness, or bodily waste) to the skin or skin dryness of wearers.

As a solution to such problems, there is proposed a lotion coating which is semisolid or solid at 20° C. and which is partially transferable to the wearer's skin, the lotion coating is applied to the liquid pervious topsheet, and the lotion transferred to the wearer's skin forms a barrier to facilitate removal of bodily waste (see Patent Publication 1).

Further, there is also known, for the purpose of reducing friction or the like, to apply a hydrophilic lotion to a topsheet of nonwoven fabric (see Patent Publication 2). The hydrophilic lotion is preferred for its hardness as a wax-like material and for avoiding reduction of liquid perviousness. In particular, a water-containing hydrophilic lotion is preferred for keeping the skin from drying.

However, there has been a problem that the effects of the water-containing hydrophilic lotion, when used with a top sheet made of discontinuous fiber nonwoven fabric, are not enhanced as much as expected.

PRIOR ART PUBLICATION

Patent Publication

Patent Publication 1: JP 2010-075733 A
Patent Publication 2: JP 2010-526630 A
Patent Publication 3: JP 2016-096926 A

SUMMARY OF THE INVENTION

Problems to be Solved by the Invention

It is therefore a primary object of the present invention to enhance the effects from application of a hydrophilic lotion to the top sheet, or the like.

Means for Solving the Problem

The present inventor, in studying nonwoven top sheets bearing a water-containing hydrophilic lotion, has acquired the following knowledge. It is conceivable that, when a water-containing hydrophilic lotion is applied to a top sheet made of discontinuous fiber nonwoven fabric, the hydrophilic lotion is prone to transfer to the member on the underside of the top sheet after the production, and is harder to be retained in the top sheet than expected, which results in a lower effect from the hydrophilic lotion than expected. The disposable wearable articles to be discussed below are based on such knowledge.

First Aspect

A disposable wearable article including:
a top sheet having a skin-touching region that is brought into contact with skin of a wearer, and
an underside member adjacent to an underside of the top sheet,
wherein the top sheet is made of liquid-pervious nonwoven fabric,
wherein the skin-touching region has a lotion-bearing zone which bears a water-containing hydrophilic lotion,
wherein the top sheet has in its under face a plurality of dents hollowed toward a top side of the top sheet and arranged at intervals,
wherein an upper surface of each dent and the underside member are spaced apart from each other with a gap therebetween, and
wherein the lotion-bearing zone at least partly overlaps one or more of the dents.

Effect

According to the present disposable wearable article, the top sheet has, in the under face of its lotion-bearing zone, a plurality of dents hollowed toward the top side of the top sheet and arranged at intervals, the upper surface of each dent and the underside member are spaced apart from each other with a gap therebetween, and the lotion-bearing zone at least partly overlaps one or more of the dents. Accordingly, the contact area between the top sheet and the underside member is reduced, so that the hydrophilic lotion applied to the top sheet hardly passes to the underside member and tends to be retained in the top sheet. In this way, the effects from application of the hydrophilic lotion to the top sheet may be enhanced more than ever. In other words, the amount of the hydrophilic lotion required for achieving the same effect may be cut down.

Second Aspect

The disposable wearable article according to the first aspect,
wherein the lotion-bearing zone has a dimension in a front-back direction of 30 mm or larger, and a dimension in a width direction of 5 mm or larger,
wherein each dent has a dimension in the front-back direction of 3 to 8 mm and a dimension in the width direction of 3 to 5 mm, and
wherein the dents are arranged all over the skin-touching region of the top sheet at intervals in the front-back direction smaller than the dimension in the front-back direction of the lotion-bearing zone and at intervals in the width direction smaller than the dimension in the width direction of the lotion-bearing zone.

Effect>

The dimensions of the lotion-bearing zone and the dimensions and arrangement of the dents may suitably be decided, but may preferably be within the ranges according to the present aspect, which allows the lotion-bearing zone to secure the areas overlapping the dents irrespective of possible slight displacement of the lotion-bearing zone due to manufacturing errors.

Third Aspect

The disposable wearable article according to the first or second aspect, wherein the top sheet is made of discontinuous fiber nonwoven fabric having a fineness of 1 to 3 dtex, a basis weight of 10 to 30 g/m², and a thickness of 0.4 to 1.4 mm, and wherein the dents have been formed in the under face of the top sheet by embossing which causes the top sheet to protrude from its underside toward its top side, and the top face of the top sheet has convexes each projecting corresponding to an inner surface of each dent, with concaves each formed between neighboring convexes.

Effect

As far as the top sheet has the dents in its under face, the top sheet in its top face may be flat without any concave or convex but, for the purpose of air permeability or reduction of surface friction, may preferably have concaves and convexes. In this case, corresponding formation of the dents in the under face and the convexes in the top face of the top sheet by embossing according to the present aspect is preferred for higher retainability of the hydrophilic lotion in the convexes, which are often brought into contact with the skin.

Further, the top sheet, when embossed in this way, may preferably be made of discontinuous fiber nonwoven fabric according to the present aspect, for clearer formation of the dents and the convexes. Furthermore, according to the present aspect, with the combination of the hydrophilic lotion and the top sheet made of discontinuous fiber nonwoven fabric, use of nonwoven fabric formed of fine fibers preferably enhances retainability of the hydrophilic lotion.

Fourth Aspect

The disposable wearable article according to any one of the first to third aspects, wherein a depth of each dent is 0.5 mm to 3 mm, wherein a dimension in the front-back direction of each dent is larger than a minimum distance between dents adjacent to each other in the front-back direction, and wherein a dimension in the width direction of each dent is larger than a minimum distance between dents adjacent to each other in the width direction.

Effect

The depth and size of the dents may suitably be decided, but a sufficiently higher area ratio of the dents than that of the rest according to the present aspect allows still superior retainability of the hydrophilic lotion in the top sheet.

Fifth Aspect

The disposable wearable article according to any one of the first to fourth aspects, wherein the hydrophilic lotion contains 70 to 90 wt % glycerin and 10 to 30 wt % water, and wherein a content of the hydrophilic lotion per unit area of the lotion-bearing zone is 5 to 15 g/m².

<Effect>

The composition of the hydrophilic lotion and the content of the lotion in the lotion-bearing zone may suitably be decided, but may preferably be within the ranges according to the present aspect.

Sixth Aspect

The disposable wearable article according to any one of the first to fifth aspects, wherein the hydrophilic lotion has a viscosity at 20° C. of 150 to 400 mPa·s.

Effect

The top sheet may preferably be made of nonwoven fabric of hydrophobic resin fibers for its low cost, which as it is has poor retainability of the water-containing hydrophilic lotion. Accordingly, it is preferred to have the viscosity of the hydrophilic lotion fall within the range according to the present aspect to enhance the hydrophilic lotion-retainability of the nonwoven fabric.

Seventh Aspect

The disposable wearable article according to any one of the first to sixth aspects, wherein the nonwoven fabric is hydrophilic fiber nonwoven fabric formed of hydrophobic resin fibers coated with a hydrophilizer.

Effect

The top sheet may preferably be made of nonwoven fabric of hydrophobic resin fibers for its low cost, which as it is has poor retainability of the water-containing hydrophilic lotion. Accordingly, in this case, it is preferred to use nonwoven fabric of hydrophilic fibers utilizing a hydrophilizer, to enhance the hydrophilic lotion-retainability of the nonwoven fabric.

Effect of the Invention

The present invention provides advantages such as enhancement of the effects from applying a hydrophilic lotion to the top sheet.

BRIEF DESCRIPTION OF THE DRAWINGS

FIG. 1 is a plan view of a tape-type disposable diaper in its spread state, illustrating the interior surface thereof.

FIG. 2 is a plan view of the tape-type disposable diaper in its spread state, illustrating the exterior surface thereof.

FIG. 3 is a cross-sectional view taken along lines 6-6 in FIG. 1.

FIG. 4 is a cross-sectional view taken along lines 7-7 in FIG. 1.

FIG. 5(a) is a sectional view taken along lines 8-8 in FIG. 1, FIG. 5(b) is a sectional view taken along lines 9-9 in FIG. 1, and FIG. 5(c) is a sectional view taken along lines 10-10 in FIG. 1.

FIG. 6 is a plan view of the top sheet and the second sheet.

FIG. 7 shows cross-sectional views of the top sheet and the second sheet.

FIG. 8 shows sectional views taken along lines 1-1, 2-2, and 3-3 in FIG. 10(*b*).

FIG. 9 shows enlarged plan views of the joining patterns of the top sheet joints.

FIG. 10 shows enlarged plan views of the joining patterns of the top sheet joints.

FIG. 11 is a plan view of a tape-type disposable diaper in its spread state, illustrating the interior surface thereof.

FIG. 12 is a plan view of a tape-type disposable diaper in its spread state, illustrating the interior surface thereof.

FIG. 13 shows plan views for explaining a specimen.

EMBODIMENTS FOR CARRYING OUT THE INVENTION

FIGS. 1 to 5 show a tape-type disposable diaper as an example of a disposable wearable article. In the figures, reference sign X refers to the overall width of the diaper exclusive of fastening tapes, whereas reference sign L refers to the overall length of the diaper. In the sectional views, dotted pattern regions represent an adhesive as joining means for joining various components. A hot melt adhesive may be applied using a known technique, such as slot application, bead application in continuous lines or dotted lines, spray application in spiral, Z, or wave shapes, or pattern coating (transfer of a hot melt adhesive by relief printing). In place of or in addition to these, fixing portions of elastic members may be fixed to adjacent members with a hot melt adhesive applied to the external surfaces thereof. Examples of the hot melt adhesive include, but not limited to, EVA-based, pressure-sensitive rubber-based (elastomer-based), polyolefin-based, and polyester/polyamide-based adhesives. The joining means for joining various components may alternatively be material melt-bonding, such as heat sealing or ultrasonic sealing.

As the nonwoven fabric in the description hereinbelow, commonly known nonwoven fabric may suitably be used depending on the parts or purposes. Examples of the constituent fibers of the nonwoven fabric include, but not limited to, synthetic fibers, such as polyolefin-based, e.g., polyethylene or polypropylene, polyester-based, or polyamide-based fibers (including not only single component fibers, but also composite fibers, such as of core/sheath type), as well as regenerated fibers, such as rayon or cupra, or natural fibers, such as cotton, and also mixtures thereof. For improved flexibility of the nonwoven fabric, the constituent fibers may preferably be crimped fibers. The constituent fibers of the nonwoven fabric may also be hydrophilic fibers (including those rendered hydrophilic with hydrophilizers), hydrophobic fibers, or water-repelling fibers (including those rendered water-repelling with water repellents). Further, nonwoven fabric may generally be categorized into discontinuous fiber nonwoven fabric, continuous fiber nonwoven fabric, spunbonded nonwoven fabric, melt blown nonwoven fabric, spunlace nonwoven fabric, thermal bonded (air through) nonwoven fabric, needle-punched nonwoven fabric, point-bonded nonwoven fabric, composite nonwoven fabric (SSS nonwoven fabric having the same or similar nonwoven layers laid one on top of another, as well as SMS or SMMS nonwoven fabric having different nonwoven layers laid one on top of another, i.e., melt blown layer interposed between spunbonded layers), or the like, generally depending on the length of the fibers, method of forming the sheet, method of joining the fibers, or layered structure, and any of these nonwoven fabric may be used. The composite nonwoven fabric refers to those having all the layers integrally manufactured and subjected to fiber joining process all over the layers, and does not include those having a plurality of nonwoven fabric layers separately manufactured and bonded with joining means, such as hot melt adhesives.

The present tape-type disposable diaper has a ventral section F extending forward of the middle of the front-back direction LD and a dorsal section B extending backward of the middle of the front-back direction LD. The present tape-type disposable diaper is configured with a crotch section M extending from forward of the middle of the product to backward of the middle of the product in the front-back direction, front wings 80 extending on opposed sides in the right-left direction at a position spaced forward of the middle of the product in the front-back direction, and back wings 81 extending on opposed sides in the right-left direction at a position spaced backward of the middle of the product in the front-back direction. Further, the present tape-type disposable diaper includes an absorber body 56 internally disposed within a region including the crotch section, a liquid-pervious top sheet 30 covering the top side of the absorber body 56, a liquid-impervious sheet 11 covering the underside of the absorber body 56, and an exterior nonwoven sheet 12 covering the underside of the liquid-impervious sheet 11 to constitute the product exterior surface.

Materials and features of each part will now be explained in turn.

Absorber Body

The absorber body 56 absorbs and holds excreted fluid, and may be formed of an assembly of fibers. Such an assembly of fibers may be a stack of discontinuous fibers of fluff pulp, synthetic fibers, or the like, as well as an assembly of filaments obtained by opening, where necessary, tows (fiber bundles) of synthetic fibers, such as cellulose acetate. The basis weight of the fibers may be about 100 to 300 g/m² for a stack of fluff pulp or discontinuous fibers, and about 30 to 120 g/m² for an assembly of filaments. The fineness of the synthetic fibers, when used, is, for example, 1 to 16 dtex, preferably 1 to 10 dtex, more preferably 1 to 5 dtex.

The plan shape of the absorber body 56 may suitably be decided, and may be in a rectangular shape or a shape having a middle portion in the front-back direction LD narrowed so as to fit around the legs. The embodiment shown in FIG. 1 has an absorber body 56, but the absorbent articles according to the present invention do not necessarily have an absorber body.

Superabsorbent Polymer Particles

The absorber body 56 may be caused partially or entirely to contain superabsorbent polymer particles. The superabsorbent polymer particles include not only "particles", but also "powders". Superabsorbent polymer particles used in this type of absorbent articles may be used as they are as the superabsorbent polymer particles here. The particle size of the superabsorbent polymer particles is not particularly limited and, for example, the particles may preferably have such a particle size that, when the particles are subjected to sieving (five-minute shaking) through a 500 μm standard sieve (JIS Z8801-1: 2006), followed by further sieving (five-minute shaking) through a 180 μm standard sieve (JIS Z8801-1: 2006) of the particles sieved through the previous sieve, the percentage of the particles remaining on the 500

μm standard sieve is wt % or less and the percentage of the particles remaining on the 180 μm standard sieve is 60 wt % or more.

Any materials of the superabsorbent polymer particles may be used without particular limitation, and those having a water absorption of 40 g/g or more are preferred. The superabsorbent polymer particles may be made of starch-based, cellulose-based, or synthetic polymer-based, and starch-acrylic acid (salt) graft copolymers, saponified products of starch-acrylonitrile copolymers, cross-linked sodium carboxymethyl cellulose, or acrylic acid (salt) polymers may be used. The superabsorbent polymer particles may preferably be in ordinary powder or granular form, but particles in other forms may also be used.

The superabsorbent polymer particles having a water absorption rate of 70 seconds or less, particularly 40 seconds or less, may preferably be used. With too slow a water absorption rate, the absorber body 56 is likely to undergo so-called back flow, wherein liquid supplied into the absorber body 56 returns out of the absorber body 56.

The superabsorbent polymer particles may preferably be those having a gel strength of 1000 Pa or higher. With such property, when the superabsorbent polymer particles are formed into a bulky absorber body 56, stickiness after liquid absorption may effectively be limited.

The basis weight of the superabsorbent polymer particles may suitably be decided depending on the absorption amount required in a use of the absorber body 56. Thus, it depends, but the basis weight may usually be to 350 g/m$^2$.

Packing Sheet

For limiting escape of the superabsorbent polymer particles, or for improving maintenance of the shape of the absorber body 56, the absorber body 56 may be wrapped with a packing sheet 58 to produce an absorbent element 50, which is to be disposed inside. The packing sheet 58 may be tissues, in particular, crepe paper, nonwoven fabric, polyethylene-laminated nonwoven fabric, perforated sheet, or the like, provided that sheets through which the superabsorbent polymer particles will not escape are preferred. When nonwoven fabric is used in place of crepe paper, hydrophilic SMMS (spunbonded/melt-blown/melt-blown/spunbonded) nonwoven fabric is particularly preferred, which may be made of polypropylene, polyethylene/polypropylene, or the like. The basis weight is preferably 5 to 40 g/m$^2$, particularly 10 to 30 g/m$^2$.

One such packing sheet 58 may be used, as shown in FIG. 3, to wrap the entire absorber body 56, or a plurality of sheets, such as an upper sheet and a lower sheet, may be used to wrap the entire absorber body 56. Alternatively, the packing sheet 58 may be omitted.

Top Sheet

The top sheet 30 extends in the front-back direction from the front end to the back end of the product, and in the width direction WD laterally beyond the absorber body 56, but its shape may suitably be modified, for example, so that the width of the top sheet 30 is shorter than the entire width of the absorber body 56, where, for example, the starting edge of a standup gather part 60 to be discussed later is located more closely to the center than each side edge of the absorber body 56 in the width direction WD, or otherwise required.

The top sheet 30 has a skin-touching region that is brought into contact with the skin of a wearer, and is preferably made of nonwoven fabric in light of liquid permeability and texture. Various nonwoven fabric may be used as the top sheet 30 but, in view of cushioning property, flexibility, permeability of loose stool (watery or muddy stool), or the like factors, discontinuous fiber nonwoven fabric, such as air-through nonwoven fabric, is preferred rather than long fiber (continuous fiber) nonwoven fabric and, usually, discontinuous fiber nonwoven fabric generally having a fineness of 1 to 10 dtex, a basis weight of 10 to 30 g/m$^2$, and a thickness of 0.4 to 1.4 mm, is preferred. The fiber length of the discontinuous fiber nonwoven fabric is not particularly limited, and is preferably about 20 to 100 mm.

Intermediate Sheet

For the purpose of immediately transferring the liquid permeated through the top sheet 30 to the absorber body, a hydrophilic intermediate sheet (also referred to as "second sheet") 40 may be provided. This intermediate sheet 40 is for immediately transferring liquid to the absorber body to improve the absorption performance thereof, and to prevent the "back-flow" phenomenon of the absorbed liquid from the absorber body. The intermediate sheet 40 of the present embodiment corresponds to the underside member adjacent to the underside of the top sheet 30, but the intermediate sheet 40 may alternatively be omitted, in which case, the packing sheet 58 is the underside member. Where the packing sheet 58 is also omitted, the absorber body 56 is the underside member.

The intermediate sheet 40 may be a liquid-pervious sheet, such as nonwoven fabric. The intermediate sheet 40 may preferably be air-through nonwoven fabric for its bulkiness. The air-through nonwoven fabric is preferably made of composite fibers of a core-clad structure, wherein the resin for the core may be polypropylene (PP), or preferably polyester (PET), which has a higher stiffness. Nonwoven fabric of such hydrophobic synthetic fibers may be transformed into hydrophilic nonwoven fabric for use, by using a commonly known hydrophilizer. The basis weight of the nonwoven fabric is preferably 17 to 80 g/m$^2$, more preferably 18 to 60 g/m$^2$. The fineness of the raw material fibers of the nonwoven fabric is preferably 2.0 to 10 dtex. For rendering nonwoven fabric bulky, it is also preferred to use eccentric fibers having off-centered cores, hollow fibers, or eccentric hollow fibers, entirely as the raw material fibers or partially mixed fibers.

In the illustrated embodiment, the intermediate sheet 40 is shorter than the absorber body 56 in width and is arranged in the center, but may be provided over the entire width of the absorber body. Further, the intermediate sheet 40 may be provided over the entire length of the diaper, or only in the middle portion in the front-back direction LD, including the excretion area, as in the illustrated embodiment.

Liquid-Impervious Sheet

The liquid-impervious sheet 11 is not particularly limited, and may preferably have moisture-permeability. As the liquid-impervious sheet 11, for example, a microporous sheet may preferably be used which is obtained by kneading an inorganic filler in a polyolefin-based resin, such as polyethylene or polypropylene, forming the resulting mixture into a sheet, and then uni- or biaxially drawing the sheet. Alternatively, the liquid-impervious sheet 11 may be made of nonwoven fabric which has been rendered waterproof.

The liquid-impervious sheet 11 preferably extends over the same or wider extent than that of the absorber body 56 in the front-back direction LD and in the width direction WD but, when another liquid-shielding means is present, may not cover the ends or edges of the absorber body 56 in the front-back direction LD and in the width direction WD, as necessary.

Exterior Nonwoven Sheet

The exterior nonwoven sheet 12 covers the entire underside of the liquid-impervious sheet 11 to impart a fabric-like appearance to the product exterior. The exterior nonwoven sheet 12 preferably has a fiber basis weight of 10 to 50 g/m², in particular 15 to 30 g/m², which, however, is not limiting. The exterior nonwoven sheet 12 may be omitted, in which case the liquid-impervious sheet 11 may be extended to the side edges of the product.

Standup Gather Part

It is preferred to provide standup gather parts 60 which stand up toward the skin of the wearer on opposed sides in the width direction WD of the top face for blocking the bodily waste moving laterally on the top sheet 30 and thereby preventing so-called side leakage. Naturally, the standup gather parts 60 may be omitted.

The standup gather parts, when employed, may be of any structure without particular limitation, and may be of any various known structures. The standup gather parts 60 in the illustrated embodiment are each composed of a gathered sheet 62 continuous substantially in the width direction WD, and elongate gathering elastic members 63 fixed in their stretched state to the gathered sheet 62 along the front-back direction LD. The gathered sheet 62 may be formed of a water-repelling nonwoven fabric, whereas the gathering elastic members 63 may be formed of a rubber thread or the like. A plurality of the elastic members may be provided on each lateral side as shown in FIGS. 1 and 2, or only one elastic member may be provided on each lateral side.

The inner face of the gathered sheet 62 has a joining start edge positioned on a lateral side portion of the top sheet 30 in the width direction WD, and the portion outward in the width direction of this joining start edge is bonded to the inner face of the corresponding side flap SF, i.e., in the illustrate embodiment, a lateral side portion of the liquid-impervious sheet 11 and a lateral side portion of the exterior nonwoven sheet 12 located laterally outward thereof in the width direction, with a hot melt adhesive or the like.

Around each leg, each standup gather part 60 is fixed to the top sheet 30 on the center side of the joining start edge in the width direction at both end portions in the product front-back direction, while the remaining portion therebetween of the standup gather part 60 is a non-fixed free portion, which will be raised by the contracting force of the elastic members 63 to be brought into close contact with the body surface.

End Flaps and Side Flaps

The tape-type disposable diaper of the illustrated embodiment has a pair of end flaps EF exclusive of the absorber body 56, extending respectively on the front and back sides of the absorber body 56, and a pair of side flaps SF exclusive of the absorber body 56, extending respectively laterally beyond the opposed sides of the absorber body 56. The side flaps SF may be formed of the main body sheet (exterior nonwoven sheet 12 or the like) continuing from the portion containing the absorber body 56, or may be formed of another material and attached.

Planar Gathers

Each side flap SF is provided with side elastic members 64, which are of elongate elastic members, such as rubber threads, and are fixed to the side flap in their stretched state in the front-back direction LD, to thereby form the round-leg portion of each side flap SF into planar gathers. The side elastic members 64 may be provided between the gathered sheet 62 and the liquid-impervious sheet 11 in the joined portion of the gathered sheet 62 in the outer vicinity in the width direction of the joining start edge as in the illustrated embodiment, or between the liquid-impervious sheet 11 and the exterior nonwoven sheet 12 in each side flap SF. A plurality of the side elastic members 64 may be provided on each lateral side as shown in the illustrated embodiment, or only one side elastic member 64 may be provided on each lateral side. Naturally, the side elastic members 64 (planar gathers) may be omitted.

The planar gathers are formed where the contracting force of the side elastic members 64 acts (in the illustrated embodiment, where the side elastic members 64 are shown). Thus, structures are conceivable, wherein the side elastic members 64 are present only in the area of the planar gathers, or wherein the side elastic members 64 extend forward or backward of the planar gathers, or both, but the contacting force of the side elastic members 64 acts only in the area of the planar gathers, while the contracting force is cancelled in the area other than the area of the planar gathers (substantially equivalent to absence of the elastic members) by finely cutting the side elastic members at one or a plurality of locations other than the area of the planar gathers, by not fixing the side elastic members 64 to the sheets between which the side elastic members 64 are interposed, or by both.

Front Wings

The present tape-type disposable diaper has front wings 80 protruding from opposed sides of the product in the right-left direction at a position spaced forward of the middle of the front-back direction of the product. The front wings may be omitted (i.e., the product may be configured such that the width of the product is not varied from its narrowest portion to the front end).

The dimension of each front wing 80 in the width direction WD may suitably be decided and, for example, may be 5 to 20% (in particular 7 to 15%) of the overall product length Y. The dimension of each front wing 80 in the width direction WD may be generally the same as the dimension of each back wing 81 to be discussed later in the width direction WD.

Back Wings

The present tape-type disposable diaper has back wings 81 protruding from opposed sides of the product in the right-left direction at a position spaced backward of the middle of the front-back direction of the product.

The dimension of each back wing 81 in the width direction WD may suitably be decided and, for example, may be the same as the dimension of each front wing in the width direction WD, or smaller or larger than the dimension of the front wing in the width direction.

Middle Section

Each lateral edge 15 of the product between the front wing 80 and the back wing 81 may have a generally linear portion passing the area of ±5 mm in the width direction on both sides of and in the direction orthogonal to a line at an acute angle of less than ±2 degrees with respect to the front-back direction LD. Each lateral edge 15 of the product between the front wing 80 and the back wing 81 may extend in a wavy or arcuate manner (not shown), or in a linear manner as in the illustrated embodiment.

Formation of Wings

As in the illustrated embodiment, by cutting out the lateral side of each side flap SF in a concave shape, the overall concaved edge may be formed which extends from the lower edge of the front wing 80, via the lateral edge 15 of the product between the front wing 80 and the back wing 81, to the lower edge of the back wing 81. In this case, the layered structure of the side flaps SF decides the layered structure of the front wings 80 and the back wings 81 and, in the illustrated embodiment, the front wings 80 and the back wings 81 are formed with gathered sheet 62 and the exterior nonwoven sheet 12. Though not shown, a front extension sheet may be provided extending laterally from each side flap SF to form all or edge-side part of each front wing 80 with the front extension sheet. Similarly, a back extension sheet may be provided extending laterally from each side flap SF to form all or edge-side part of each back wing 81 with the back extension sheet. The front extension sheet and the back extension sheet may be formed of various nonwoven fabric.

Fastening Part

Each back wing 81 is provided with a fastening part 13A to be detachably attached to the ventral section F when the product is worn. That is, in fitting the product, the opposed lateral side portions of the back wings 81 are brought onto the ventral side of the wearer, and the fastening parts 13A of the back wings 81 are attached to the exterior face of the ventral section F. Each fastening part 13A may be a hook member (male part) of a mechanical fastener (hook and loop fastener), or a pressure-sensitive adhesive layer. The hook member has a number of engaging projections on its attaching surface, and the engaging projections may be in various known shapes, such as tick-shaped, J-shaped, mushroom-shaped, T-shaped, or double J-shaped (wherein J-shaped parts are joined back to back).

The fastening part 13A may directly be attached to the back wing 81, or a fastening tape 13 having the fastening part 13A may be attached to the back wing 81, as in the illustrated embodiment. The structure of the fastening tape 13 is not particularly limited and, in the illustrated embodiment, may have a tape attachment portion 13C fixed to the side flap SF, a tape body 13B protruding from the tape attachment portion 13C, and the fastening part 13A disposed in the middle of the tape body 13B in the width direction WD, and the portion beyond this fastening part 13A is a grip portion. The sheet material forming from the tape attachment portion 13C to the tape body 13B may be nonwoven fabric, plastic film, polyethylene-laminated nonwoven fabric, paper, or composites thereof.

Fastening sites on the exterior face of the ventral section F to which the fastening parts 13A are to be connected, may suitably be decided, and only the body section located between the right and left front wings 80 may provide the fastening sites, or the areas each extending from a lateral side portion of the body section toward the proximal side of the front wing 80 may provide the fastening sites. It is preferred that such fastening sites are rendered easy to be engaged by the fastening parts 13A, and may be provided with a target sheet 24 having targets for facilitating fastening. For example, when the fastening parts 13A are hook members (male parts) of mechanical fasteners (hook and loop fasteners), the fastening sites on the exterior face of the ventral section F may be formed with a loop member (female part) of mechanical fasteners, or nonwoven fabric. As such a loop member, a plastic film stitched with a loop yarn is known, but in view of air permeability and flexibility, preferred is continuous fiber nonwoven fabric of which continuous fiber direction is its width direction WD (such as spunbonded nonwoven fabric generally having a fineness of 2.0 to 4.0 dtex, a basis weight of 20 to 50 g/m², and a thickness of 0.3 to 0.5 mm), provided with melt-bonded portions wherein fibers are melt-bonded with each other intermittently at least in the width direction WD. When a region of the exterior face of the ventral section F including the fastening sites is formed with the exterior nonwoven sheet 12 as in the illustrate embodiment, the hook members may be fastened to the exterior nonwoven sheet 12 without any other means added thereto. A loop member 20 may be adhered only to each fastening site on the exterior face of the ventral section F. Further, when the fastening parts 13A are in the form of pressure-sensitive adhesive layers, a plastic film having a smooth surface which facilitates strong adhesion thereon may be attached to the fastening sites on the exterior face of the ventral section F.

Fixing of Top Sheet

The top sheet 30 is preferably bonded, via a hydrophobic hot melt adhesive 29, to an underside member arranged on the underside of the top sheet 30. Instead of or in addition to this, the top sheet 30 may be joined to an underside member arranged on the underside of the top sheet 30 by melting of at least one of the top sheet 30 and the underside member arranged on the underside of the top sheet 30. The area in which the top sheet 30 is fixed to the underside member may be all over the top sheet 30, or the area of the underside member in contact with the top sheet 30 other than the dents 20. The underside member includes the intermediate sheet 40, the packing sheet 58, and the liquid-impervious sheet 11 in the illustrated embodiment, but is not limited thereto.

The hydrophobic hot melt adhesive 29 may be EVA-based, polyolefin-based, or polyester/polyamide-based adhesive or the like, and a pressure-sensitive rubber-based (elastomer-based) adhesive is particularly preferred.

The amount of the hydrophobic hot melt adhesive 29 to be applied may suitably be decided, and may usually be about 0.1 to 10 g/m². In particular, with the amount of the hydrophobic hot melt adhesive 29 being about 0.5 to 5 g/m², the hot melt adhesive 29 may preferably be kept from sticking out into the dents 20, but interference with a hydrophilic lotion in bonding as will be discussed later is likely to occur, so that it is preferred to combine the application amount with designing of the application pattern of the hydrophilic lotion, or the like. The application pattern of the hydrophobic hot melt adhesive 29 may suitably be decided, and may preferably be a dense pattern with minute non-applied portions scattered all over (by spray application in spiral, Z, or wave shapes, or the like), or may be a continuous surface such as by slot application.

Lotion-bearing Zone

The skin-touching region of the top sheet 30 has lotion-bearing zones 32 which bear a water-containing hydrophilic lotion, as shown in FIGS. 7, 11, and 12. With too small dimensions of each lotion-bearing zone, the friction-reducing effect is localized, which provides little significance in protection of the skin of a wearer, so that each lotion-bearing zone 32 preferably has a machine direction (MD: the front-back direction LD in the illustrated embodiment) dimension 32L of 30 mm or more and a cross direction (CD: the width direction WD in the illustrated embodiment) dimension 32W of 5 mm or more. The MD dimension 32L of the lotion-bearing zone 32 is more preferably 50 mm or more, and particularly preferably 100 mm or more. The upper limit of the MD dimension 32L of the lotion-bearing zone 32 is the overall product length L, but may be shorter than this. The CD dimension 32W of the lotion-bearing zone 32 is more preferably 10 mm or more. The upper limit of the CD dimension 32W of the lotion-bearing zone 32 is the dimension in the width direction WD of the top sheet 30, but may be shorter than this.

Only one lotion-bearing zone 32 having a relatively large area may be provided in one location, or a plurality of lotion-bearing zones may be provided in a plurality of locations. The lotion-bearing zones 32 may preferably be provided in a vertical-striped pattern as in the illustrated embodiment, or in a horizontal-striped pattern. In such cases, the intervals 32X of the adjacent lotion-bearing zones 32 may suitably be decided, and may preferably be, for example, about 1.5 to 10 mm.

The nonwoven fabric for the top sheet 30 may preferably be discontinuous fiber nonwoven fabric having a fineness of 1 to 3 dtex (more preferably 1.5 to 2.5 dtex), a basis weight of 10 to 30 g/m² (more preferably 15 to 25 g/m²), and a thickness of 0.4 to 1.4 mm (more preferably 0.5 to 1.0 mm). That is, with such discontinuous fiber nonwoven fabric, fineness of the fibers contributes to reduction of surface friction, which, in cooperation with the friction-reducing effect of the hydrophilic lotion, improves the overall friction-reducing effect. In addition, the fineness of the fibers also improves the hydrophilic lotion-retainability, which further improves the friction-reducing effect. More specifically, by the combination of the discontinuous fiber nonwoven fabric and the hydrophilic lotion, the lotion-bearing zones of the top sheet 30 preferably have an average coefficient of friction MIU of 0.2 to 0.4.

The surface moisture percentage of the lotion-bearing zones 32 is not particularly limited, and may preferably be 3 to 10%, particularly 4 to 8%, for moderately moistening and keeping the skin of a wearer from drying.

The hydrophilic lotion, as long as it contains water, may have any ingredient composition but water. For example, the components other than water of the hydrophilic lotion may be one or a plurality of members selected from glycerin, propylene glycol, dipropylene glycol, 1,3-butylene glycol, polyethylene glycol, sorbitol, xylitol, and sodium pyrrolidone carboxylate; and further sugars, such as trehalose, mucopolysaccharides (e.g., hyaluronic acid and derivatives thereof, chondroitin and derivatives thereof, heparin and derivatives thereof, or the like), elastin and derivatives thereof, collagen and derivatives thereof, NMF-related materials, lactic acid, urea, higher fatty acid octyldodecyl esters, seaweed extracts, Bletilla Striata root extract, various amino acids and derivatives thereof, and the like. The hydrophilic lotion may further contain one or a plurality of additives selected from the group consisting of emulsifiers, phosphates, paraffin, and surfactants. The surfactants may preferably be ether-type nonionic surfactants or nonionic surfactants including EO/PO-type. For improved product storage stability, the hydrophilic lotion may contain a preservative but, as the hydrophilic lotion is to be transferred to the skin for moistening the same, it is more preferred that the hydrophilic lotion is free of preservatives.

A particularly preferred hydrophilic lotion contains 70 to 90 wt % glycerin and 10 to 30 wt % water. Such a hydrophilic lotion mainly composed of glycerin with a moderate amount of water, is preferred not only as a moisturizer when transferred to the skin, but also for its hardness to decay as the water is held in the glycerin as bound water (glycerin has an extremely high water retainability). That is, for using a water-containing hydrophilic lotion in this context, it is preferred to contain a large amount of glycerin, to ensure a sufficient surface moisture percentage (e.g., 3 to 10% as discussed above), and to keep a water activity value of the hydrophilic lotion low, for example, 0.8 or lower, more preferably 0.3 to 0.7, particularly preferably 0.3 to 0.5, so that, even in the absence of a preservative, development of microorganisms may be suppressed to provide improved shelf life, and the moisturizing effect upon transfer to the skin may be improved.

The content of the hydrophilic lotion in the lotion-bearing zones 32 may suitably be decided depending on the purpose. For example, with a hydrophilic lotion containing 70 to 90 wt % glycerin and 10 to 30 wt % water, the content of the hydrophilic lotion per unit area of the lotion-bearing zones 32 is preferably 5 to 15 g/m². When a plurality of zones with different contents of the hydrophilic lotion is present as referred to by 32a and 32b in FIG. 12, or when the applied amount of the hydrophilic lotion varies gradually, it is preferred that the content of the hydrophilic lotion all over the lotion-bearing zones is 2 to 20 g/m², the content of the hydrophilic lotion is 5 to 15 g/m² in 20% or more of the area of the lotion-bearing zones 32, or both.

Note that the content of glycerin is measured in accordance with the following method for measuring glycerin content.

Method for Measuring Glycerin Content

Four pieces of the same product are provided, and any one of them is subjected to measurement of the dimensions of the glycerin-bearing zones 32 in accordance with the method as will be discussed later, to thereby find the area of the glycerin-bearing zones 32 (where the product has a plurality of glycerin-bearing zones, the total area).

All the glycerin-bearing zones 32 are cut out of the top sheets 30 of the four pieces of the same product (the glycerin-bearing zones may not necessarily be cut out precisely along their edges, but areas around the glycerin-bearing zones may somewhat be included, as far as the entire glycerin-bearing zones are included), and all of them are used as specimens, or the top sheets 30 of the four pieces of the same product are taken out and used as they are as specimens.

The specimens are placed in a 300 ml beaker containing water at 25° C., randomly crushed or muddled with a glass rod repeatedly for 1 minutes or longer, and left to stand for 60 minutes in a state of being soaked in water. During the standing, in order to keep the height of the specimens in the beaker as low as possible, the specimens are folded and placed under a weight, or fixed by bonding or sewing in a folded state. The amount of the water is the minimum for soaking the entire specimens therein (e.g., 10 ml). After the standing, the specimens are randomly crushed or muddled with a glass rod repeatedly for 1 minutes or longer, lifted and squeezed sufficiently. The glycerin-containing water left in the beaker is subjected to measurement of the glycerin concentration using a glycerin concentration meter. Further, the weight of the glycerin-containing water left in the beaker is also measured. Based on the results of the measurements, the weight of glycerin contained in the glycerin-containing water is determined.

The weight of glycerin in the glycerin-containing water is divided by four times the area of the glycerin-bearing zones 32 (for four pieces of the product), to determine the glycerin content (g/m$^2$) of the glycerin-bearing zones 32.

The top sheet 30 may preferably be formed of hydrophobic resin fibers for their low cost, which as they are have poor retainability of the water-containing hydrophilic lotion. Thus, the hydrophilic lotion preferably has a viscosity at 20° C. of 150 to 400 mPa·s. In this way, the hydrophilic lotion-retainability of the top sheet 30 is preferably enhanced.

The top sheet 30 is preferably formed of hydrophobic resin fibers for their low cost, which as they are have poor retainability of the water-containing hydrophilic lotion. Thus, it is preferred to use, as the top sheet 30, hydrophilic fiber nonwoven fabric formed of hydrophobic resin fibers coated with a hydrophilizer. In this way, the hydrophilic lotion-retainability of the top sheet 30 is preferably enhanced.

The hydrophilizer may preferably be, in consideration of safety for human body, safety in process, or the like factors, one or a mixture of nonionic activators obtained by addition of ethylene oxide to higher alcohols, higher fatty acids, alkylphenols, or the like, or anionic activators, such as alkyl phosphates (octyl or dodecyl) or alkyl sulfates. The amount to be applied may vary depending on the required performance, but may usually preferably be about 0.1 to 2.0 wt %, particularly about 0.2 to 1.0 wt % of the dry weight of the objective sheet. Note that the hydrophilizer may similarly be applied to the intermediate sheet.

Dent

As shown in FIGS. 6 to 8, the top sheet 30 has in its under face a plurality of dents 20 hollowed toward the top side of the top sheet 30 and arranged at intervals, the upper surface of each dent 20 and the underside member (intermediate sheet 40 in the illustrate embodiment) are spaced apart from each other with a gap therebetween, and each lotion-bearing zone 32 at least partly overlaps the dents 20. In this way, the contact area between the top sheet 30 and the underside member is reduced, and the hydrophilic lotion applied to the top sheet 30 is hard to transfer to the underside member and is likely to remain in the top sheet 30, which enhances the effect from application of the hydrophilic lotion to the top sheet. In other words, the amount of the hydrophilic lotion required for achieving the same effect may be cut down.

The depth 20$h$ of the dents 20 may suitably be decided, and is usually preferably 0.5 mm to 3 mm for the purpose of more reliably reducing the contact area between the top sheet 30 and the underside member.

The dimensions of the lotion-bearing zones 32 and the dimensions and arrangement of the dents 20 may suitably be decided. For example, when each lotion-bearing zone 32 has a dimension of 30 mm or larger in the front-back direction LD and a dimension of 5 mm or larger in the width direction WD, each dent 20 preferably has a dimension 20$q$ of 3 to 8 mm in the front-back direction and a dimension 20$w$ of 3 to 5 mm in the width direction WD, and the dents 20 are arranged over the skin-touching region of the top sheet 30 at intervals in the front-back direction LD shorter than the dimension of each lotion-bearing zone 32 in the front-back direction LD and at intervals in the width direction WD shorter than the dimension of each lotion-bearing zone 32 in the width direction WD. This securely allows the lotion-bearing zones 32 to have the areas overlapping the dents 20, even when the lotion-bearing zones 32 are somewhat displaced due to manufacturing errors or the like factors.

Further, with the dimension 20$q$ in the front-back direction LD of each dent 20 being larger than the minimum distance 20$p$ between the dents 20 adjacent to each other in the front-back direction LD (20$q$>20$p$), and the dimension 20$w$ in the width direction WD of each dent 20 being larger than the minimum distance 20$i$ between the dents adjacent to each other in the width direction WD (20$w$>20$i$), the area percentage of the dents (percentage of the area of the dents per unit area of the top sheet) is sufficiently higher than that of the remaining region except for the dents 20, so that the hydrophilic lotion-retainability of the top sheet 30 is further preferably enhanced.

The plan shape of each dent 20 is not particularly limited, and may be of any arbitrary shape, such as circular as in the illustrated embodiment, elliptical, triangular, rectangular, polygonal with five or more vertices, star-shaped, cloud-shaped, or the like.

The plan arrangement of the dents 20 is not particularly limited, and may suitably be modified, like arrangement in matrices as shown in FIG. 9, or staggered arrangement (staggered in the adjacent rows) as shown in FIGS. 6 and 10.

In the illustrate embodiment, it is envisaged that the dents 20 are arranged almost all over the top sheet 30, but the dents 20 may be provided only in a part of the top sheet 30, as long as the lotion-bearing zones 32 at least partly overlap the dents 20. For example, when the intermediate sheet 40 is shorter than the top sheet 30, the dents 20 may be provided only almost all over the overlapping area of the top sheet 30 and the intermediate sheet 40.

As far as the dents 20 are provided in the under face of the top sheet 30, the top face of the top sheet 30 may be flat without any concave or convex as shown in FIG. 7, but in view of air permeability and reduction of surface friction of the top sheet 30, the top face of the top sheet 30 is preferably provided with concaves and convexes as shown in FIGS. 6 and 8 to 10. Such concaves and convexes may be formed by embossing. In particular, as in the illustrated embodiment, when the dents 20 are formed by embossing by pressing the top sheet 30 from its underside toward its top side, seen from the top face side of the top sheet 30, convexes 31 are formed in the arrangement corresponding to (aligned to) the arrangement of the dents in the under face of the top sheet 30. This preferably enhances the hydrophilic lotion-retainability at the convexes 31, which are often brought into contact with the skin. Note that, in subjecting the top sheet 30 to such embossing, use of the top sheet 30 made of discontinuous fiber nonwoven fabric as discussed above preferably results in more definite formation of the dents 20 and the convexes 31 and enhanced hydrophilic lotion-retainability. It should be understood that the reference numeral 33 refers to the area between the neighboring convexes 31, i.e., a concave as seen from the top side.

One preferred example is that, as shown in FIGS. 6 and 8-10, the top sheet 30 in the areas between the convexes 31 (as seen from the underside, the areas between the dents adjacent to each other in the width direction or in the front-back direction is joined to the intermediate sheet 40 by pressure melt-bonding, to thereby form a number of top sheet joints 82 arranged in an intermittent joint pattern in the width direction and in the front-back direction. The top sheet joints 82 also provide the bottom of each concave. In the joint pattern of the top sheet 30 and the intermediate sheet 40, in each area between the convexes 31 adjacent to each other in the machine direction (MD), a row of a plurality of top sheet joints 82 arranged at intervals in the cross direction (CD) is formed to pass the center in the CD of that area, while in each intermediate portion between the top sheet joints 82 adjacent to each other in the CD, the top sheet 30 and the intermediate sheet 40 are not melt-bonded, and the top sheet 30 is compressed compared to both sides in the MD of the intermediate portion to form a compressed portion 83. This structure may be produced according to the method disclosed in Patent Publication 3.

In the compressed portions 83, as long as the top sheet is compressed, the intermediate sheet 40 may or may not be compressed integrally with the top sheet 30. Further, in the areas other than the top sheet joints 82 and the compressed portions 83, the top sheet 30 and the intermediate sheet 40 are not melt-bonded and may be compressed as in the CD intermediate portion, but preferably the top sheet 30 and the intermediate sheet 40 are not melt-bonded and the top sheet 30 is less compressed (including non-compression where the top sheet 30 is not at all compressed) compared to the CD intermediate portions. That is, in the top sheet 30, referring to the thickness of the top sheet joints 82 as T1, the thickness of the compressed portions 83 as T2, and the thickness of the areas other than the top sheet joints 82 and the compressed portions 83 as T3, the relation among the three may be T1<T2=T3, but is preferably T<T2<T3.

The shape of each top sheet joint 82 is not particularly limited, and may be any arbitrary shape, such as circular as in the illustrated embodiment, elliptical, polygonal, star-shaped, or cloud-shaped.

As shown in FIG. 7(*c*), the lotion-bearing zones 32 may be provided only where the dents 20 are formed in the top sheet 30. In other words, a number of lotion-bearing zones 32 may be provided corresponding to the arrangement of the dents 20. It is indisputable that, where the convexes 31 are formed in the top face of the top sheet 30 corresponding to the dents 20 in the under face of the top sheet 30 as in the embodiments shown in FIGS. 6, 8 to 10, the lotion-bearing zones 32 may also be provided only where the dents 20 are formed in the top sheet 30, i.e., only on the convexes 31, though not shown.

<Explanation of Terms in the Specification>

The following terms appearing in the present specification shall have the following means unless otherwise specified herein.

The "front-back direction" refers to the direction shown by the reference sign LD (longitudinal direction) in the figures, whereas the "width direction" refers to the direction shown by the reference sign WD (right-left direction) in the figures, and the front-back direction and the width direction are orthogonal to each other.

The "machine direction (MD)" and "cross direction (CD)" refer to the flow direction (MD) and the lateral direction orthogonal thereto (CD) in the production facilities, respectively, and either one of these is aligned to the front-back direction while the other is aligned to the width direction, depending on the parts of the product. The MD of nonwoven fabric is the direction of fiber orientation in the nonwoven fabric. The fiber orientation refers to the direction along which the fibers of the nonwoven fabric are aligned, and may be identified, for example, by a measurement method pursuant to the fiber orientation testing method using zero-span tensile strength prescribed in TAPPI Standard Method T481, or by a simplified measurement method for determining the fiber orientation by the ratio of tensile strengths in the front-back direction and in the width direction.

The "top side" refers to the side, when the article is worn, closer to the skin of the wearer, whereas the "underside" refers to the side, when the article is worn, away from the skin of the wearer.

The "top face" refers to the face, when the article is worn, closer to the skin of the wearer, whereas the "under face" refers to the face, when the article is worn, away from the skin of the wearer.

The "area ratio" refers to the ratio of the objective area per unit area, and is calculated by dividing the sum of the areas of objective portions (e.g., apertures) in an objective region (e.g., cover nonwoven sheet) by the area of that objective region, and is represented in percentage. In a configuration where a number of objective portions are provided at intervals, the area ratio is preferably determined with the objective region being set to a size containing 10 or more objective portions. For example, the area ratio of the apertures may be determined in the following procedure, using, for example, VHX-1000 (trade name) manufactured by KEYENCE under the measurement conditions in ×200 magnification.

(1) Place a specimen under a ×20 magnification lens, and adjust the focus. Position the nonwoven fabric so that 4×6 apertures are in the field.

(2) Specify the brightness of the aperture portions, and measure the area of the apertures.

(3) Click the color extraction in "Area Measurement" under "Measurement and Comment". Click the aperture portions.

(4) Click "Collective Measurement", check "Display measurement result window", and store in CSV data.

The "stretch rate" refers to a value with respect to the natural length being 100%. For example, a 200% stretch rate is synonymous with stretch in two folds.

The "gel strength" is determined as follows. To 49.0 g of artificial urine (a mixture of 2 wt % urea, 0.8 wt % sodium chloride, 0.03 wt % calcium chloride dihydrate, wt % magnesium sulfate heptahydrate, and 97.09 wt % ion-exchanged water), 1.0 g of superabsorbent polymer is added and stirred with a stirrer. The resulting gel is left in a chamber with constant temperature and humidity at 40° C. at 60% RH for 3 hours, and then the temperature is returned to the ordinary temperature. The gel strength is measured in a curd meter (Curdmeter-MAX ME-500 manufactured by I. techno Engineering).

The "basis weight" is determined as follows. A specimen or test piece is preliminarily dried, left in a laboratory or in apparatus under the standard conditions (23±1° C. temperature and 50±2% relative humidity in the testing location) until constant mass is attained. The preliminary drying refers to attaining constant mass from a specimen or test piece in the environment at a temperature of 100° C. No preliminary drying may be performed on fibers with an official regain of 0.0%. From the test piece of the constant mass, a specimen of 100 mm×100 mm size is cut out using a sampling template (100 mm×100 mm). The weight of the specimen is measured and multiplied by 100 times to calculate the weight per square meter, which is taken as the basis weight.

The "thickness" is automatically measured using an automatic thickness meter (KES-G5 handy compression tester program) under a load of 0.098 N/cm² with the compression area of 2 cm 2. The thickness of perforated nonwoven fabric is measured at a position other than the apertures and the protrusions therearound.

The water absorption is determined in accordance with JIS K7223—1996 "Testing method for water absorption capacity of super absorbent polymers".

The water absorption rate is defined as the "time spent until the end point is reached" in carrying out JIS K7224—1996 "Testing method for water absorption rate of super absorbent polymers" using 2 g of superabsorbent polymer and 50 g of saline.

The "spread state" refers to the state in which an article is spread flatly without contraction (including any contraction, such as contraction by means of elastic members) or slack.

The size of each part refers to the size not in the natural length state but in the spread state, unless otherwise specified.

The "melt viscosity" is determined at a prescribed temperature using a Brookfield B-type viscometer (spindle No. 027) in accordance with JIS Z 8803.

The "maximum dimension" of an aperture refers to the longer of the MD dimension and the CD dimension.

The "average coefficient of friction MIU" and the "variation deviation of average coefficient of friction MMD" is determined using a friction tester KES-SE manufactured by KATO TECH CO., LTD. (10 mm square silicon sensor, 50 g load), and refers to the value measured for the sensor moving distance of 20 mm. The sensor moving direction (direction of friction) is the MD of the top sheet. When a product is to be subjected to the measurement, members constituting the product except for the top sheet are removed or cut out to the extent that the friction test on the top sheet surface would not be affected (as such, members, for example, melt-bonded to the top sheet will not be removed), and the test is conducted on the top sheet in its spread state.

In addition, when the CD dimension of a lotion-bearing zone on the top sheet is less than the sensor dimension (10 mm), the top sheet 30 is cut along the lateral edges of the lotion-bearing zone 32 as shown in FIG. 13(a) to obtain a specimen 300 solely of the lotion-bearing zone 32 (narrower in width than the sensor 100), and this specimen is subjected to measurement with the center of the sensor 100 being aligned to the center of the specimen 300 in the CD as shown in FIG. 13(b). In every measurement, the hydrophilic lotion remaining on the surface of the sensor 100 is thoroughly wiped off before next measurement.

The lotion-bearing zones, if cannot be identified visually, may be identified through appropriate measures. For example, a necessary number of specimens (for measurement and for positional identification) are provided, which have the lotion-bearing zones 32 at the same positions, the lotion-bearing zones 32 on the top sheet 30 of a specimen for positional identification are colored with an appropriate coloring agent in a color different from that of the surroundings, the colored areas are identified using a ruler or other proper image measurement device, and then the measurement is made on a specimen for measurement at the same positions as those of the colored areas identified in the specimen for positional identification, which positions are regarded as the lotion-bearing zones 32. For coloring the lotion-bearing zones 32, a water leak testing agent MORAY-MILLE W manufactured by TASETO CO., LTD. may preferably be used. The lotion-bearing zones 32 may be identified by this process also for measurement of the MD dimension 32L and CD dimension 32W of a lotion-bearing zone 32, or for determination of surface moisture percentage to be discussed below.

The "surface moisture percentage" is an average calculated from the values measured at three arbitrary positions in the lotion-bearing zones 32 using a moisture checker MY-808S manufactured by SCALAR CORPORATION. Note that in every measurement, the hydrophilic lotion remaining on the measuring surface of the moisture checker is thoroughly wiped off before next measurement.

The "water activity value" may be determined using an electric resistance-type water activity meter, such as EZ-100 ST (electric resistance type) manufactured by FREUND CORPORATION. Before measurement, calibration is performed with a saturated solution. Measurement may be made according to an electric resistance-type test based on Standard Methods of Analysis in Food Safety Regulation. Specifically, a sample is taken in a volume of 3% or more the inner capacity of the detector of the water activity meter, placed on an aluminum foil dish or an open flat plate, immediately introduced into and sealed in the detector, and subjected to the conditions of 25±2° C. The values are read every 10 minutes and, when fluctuation of the value is no longer observed, the water vapor pressure in the detector is regarded as in equilibrium, and the value at that point is taken as the measured value of that sample. Each sample is measured three times, and the average of the three measured values is taken as the water activity value.

The "viscosity" is determined at a prescribed temperature using a Brookfield B-type viscometer (spindle No. 027) in accordance with JIS Z 8803.

A test or measurement shall be, in the absence of description about environmental conditions, performed in a laboratory or in apparatus under the standard conditions (23±1° C. temperature and 50±2% relative humidity in the testing location).

INDUSTRIAL APPLICABILITY

The present invention is applicable not only to underpants-type disposable diapers or tape-type disposable diapers, but also to general disposable wearable articles, such as pad-type disposable diapers, disposable swim wears, diaper covers, or sanitary napkins.

DESCRIPTION OF REFERENCE SIGNS

11: liquid-impermeable sheet
12: exterior nonwoven sheet
20: dent
30: top sheet
40: intermediate sheet

50: absorbent element
56: absorber body
58: packing sheet
60: standup gather part
62: gathered sheet
LD: front-back direction
WD: width direction
29: hydrophobic hot melt adhesive
31: convex
32: lotion-bearing zone

The invention claimed is:

1. A disposable wearable article comprising:
a top sheet having a skin-touching region that is configured to be brought into contact with skin of a wearer, and
an underside member adjacent to an underside of the top sheet,
wherein the top sheet is made of liquid-pervious nonwoven fabric,
wherein the skin-touching region has a lotion-bearing zone which bears a water-containing hydrophilic lotion,
wherein the top sheet has in its under face a plurality of dents hollowed toward a top side of the top sheet and arranged at intervals, and wherein the top sheet in its top face has minimal concave or convex deviation from a single plane,
wherein an upper surface of each dent and the underside member are spaced apart from each other with a gap therebetween,
wherein the lotion-bearing zone at least partly overlaps one or more of the dents,
wherein a dimension in a front-back direction of each dent is larger than a minimum distance between dents adjacent to each other in the front-back direction, and
wherein a dimension in a width direction of each dent is larger than a minimum distance between dents adjacent to each other in the width direction.

2. The disposable wearable article according to claim 1, wherein the lotion-bearing zone has a dimension in the front-back direction of 30 mm or larger, and a dimension in the width direction of 5 mm or larger,
wherein each dent has a dimension in the front-back direction of 3 to 8 mm and a dimension in the width direction of 3 to 5 mm, and
wherein the dents are arranged all over the skin-touching region of the top sheet at intervals in the front-back direction smaller than the dimension in the front-back direction of the lotion-bearing zone and at intervals in the width direction smaller than the dimension in the width direction of the lotion-bearing zone.

3. The disposable wearable article according to claim 2, wherein the hydrophilic lotion comprises 70 to 90 wt % glycerin and 10 to 30 wt % water, and
wherein a content of the hydrophilic lotion per unit area of the lotion-bearing zone is 5 to 15 $g/m^2$.

4. The disposable wearable article according to claim 2, wherein the hydrophilic lotion has a viscosity at 20° C. of 150 to 400 mPa·s.

5. The disposable wearable article according to claim 2, wherein the nonwoven fabric is hydrophilic fiber nonwoven fabric formed of hydrophobic resin fibers coated with a hydrophilizer.

6. The disposable wearable article according to claim 1, wherein the top sheet is made of discontinuous fiber nonwoven fabric having a fineness of 1 to 3 dtex, a basis weight of 10 to 30 g/m2, and a thickness of 0.4 to 1.4 mm, and
wherein the dents have been formed in the under face of the top sheet by embossing which causes the top sheet to protrude from its underside toward its top side, and the top face of the top sheet has convexes each projecting corresponding to an inner surface of each dent, with concaves each formed between neighboring convexes.

7. The disposable wearable article according to claim 6, wherein the hydrophilic lotion comprises 70 to 90 wt % glycerin and 10 to 30 wt % water, and
wherein a content of the hydrophilic lotion per unit area of the lotion-bearing zone is 5 to 15 $g/m^2$.

8. The disposable wearable article according to claim 6, wherein the hydrophilic lotion has a viscosity at 20° C. of 150 to 400 mPa·s.

9. The disposable wearable article according to claim 6, wherein the nonwoven fabric is hydrophilic fiber nonwoven fabric formed of hydrophobic resin fibers coated with a hydrophilizer.

10. The disposable wearable article according to claim 1, wherein a depth of each dent is 0.5 mm to 3 mm.

11. The disposable wearable article according to claim 10, wherein the hydrophilic lotion comprises 70 to 90 wt % glycerin and 10 to 30 wt % water, and
wherein a content of the hydrophilic lotion per unit area of the lotion-bearing zone is 5 to 15 $g/m^2$.

12. The disposable wearable article according to claim 10, wherein the hydrophilic lotion has a viscosity at 20° C. of 150 to 400 mPa·s.

13. The disposable wearable article according to claim 10, wherein the nonwoven fabric is hydrophilic fiber nonwoven fabric formed of hydrophobic resin fibers coated with a hydrophilizer.

14. The disposable wearable article according to claim 1, wherein the hydrophilic lotion comprises 70 to 90 wt % glycerin and 10 to 30 wt % water, and
wherein a content of the hydrophilic lotion per unit area of the lotion-bearing zone is 5 to 15 $g/m^2$.

15. The disposable wearable article according to claim 14, wherein the hydrophilic lotion has a viscosity at 20° C. of 150 to 400 mPa·s.

16. The disposable wearable article according to claim 14, wherein the nonwoven fabric is hydrophilic fiber nonwoven fabric formed of hydrophobic resin fibers coated with a hydrophilizer.

17. The disposable wearable article according to claim 1, wherein the hydrophilic lotion has a viscosity at 20° C. of 150 to 400 mPa·s.

18. The disposable wearable article according to claim 17, wherein the nonwoven fabric is hydrophilic fiber nonwoven fabric formed of hydrophobic resin fibers coated with a hydrophilizer.

19. The disposable wearable article according to claim 1, wherein the nonwoven fabric is hydrophilic fiber nonwoven fabric formed of hydrophobic resin fibers coated with a hydrophilizer.

\* \* \* \* \*